United States Patent [19]
Kandimalla et al.

[11] Patent Number: 5,739,308
[45] Date of Patent: Apr. 14, 1998

[54] INTEGRATED OLIGONUCLEOTIDES

[75] Inventors: Ekambar R. Kandimalla, Worcester; Sudhir Agrawal, Shrewsbury, both of Mass.

[73] Assignee: Hybridon, Inc., Cambridge, Mass.

[21] Appl. No.: 418,123

[22] Filed: Apr. 6, 1995

Related U.S. Application Data

[63] Continuation of Ser. No. 248,636, May 24, 1994, abandoned, which is a continuation of Ser. No. 8,000, Jan. 21, 1993, abandoned.

[51] Int. Cl.$^6$ .................................................. C07H 21/04
[52] U.S. Cl. .................... 536/24.5; 536/23.1; 536/24.1
[58] Field of Search ................................. 536/23.1, 24.5, 536/24.1; 514/44

[56] References Cited

U.S. PATENT DOCUMENTS

| | | |
|---|---|---|
| 4,689,320 | 8/1987 | Kaji . |
| 5,015,570 | 5/1991 | Scangos et al. . |
| 5,107,065 | 4/1992 | Shewmaker et al. . |
| 5,149,748 | 9/1992 | Shimizu et al. . |
| 5,194,428 | 3/1993 | Agrawal et al. . |

FOREIGN PATENT DOCUMENTS

| | | |
|---|---|---|
| 0227976 | 7/1987 | European Pat. Off. . |
| WO9106626 | 5/1991 | WIPO . |

OTHER PUBLICATIONS

Helene, The antigene strategy: control of gene expression by triplex–forming–oligonucleotides, Anti–Cancer Drug Design, vol. 6, pp. 569–584, 1991.
Manzini, G. et al., *J. Molec. Biol.* 213:833–843 (1990).
Xodo, L. et al., *J. Molec. Biol.* 205:777–781 (1989).
Hélène, C. *Anti Cancer Drug Design* 6:569–584 (1991).
Xodo, L.E. et al., *Nucleic Acids Res.* 18:3557–3564 (1990).
Stein et al, Science, v. 261, 8:20–93, pp. 1004–10012.
Giovannangeli et al, J. Am. Chem. Soc., v. 113, 1991, pp. 7775–7777.
D'Souza et al, J. Biomolecular Structure & Dynamics, v. 10, 1992, pp. 141–152.
Zimmerman et al., *J. Mol. Biol.* 92:181–192 (1975).
Zamecnik et al., *Proc. Natl. Acad. Sci.* (USA) 75:280–284 (1978).
Richards et al., *Virology* 89:395–408.
Harris et al., *J. Virol.* 36:659–664.
Lee et al., *Nucleic Acids Res.* 8:4305–4320.
Campbell et al., *Nature* 311:350–355 (1984).
Rice et al., *Science* 229:726–733.
Robertson et al., *J. Virol.* 54:651–660 (1985).
Davison et al., *J. Gen. Virology* 67:2279–2286 (1986).
Cooney et al., *Science* 241:456–459 (1988).
Praseuth et al., *Proc. Natl. Acad. Sci.* (USA) 85:1349–1353 (1988).
Sen et al., *Nature* 334:364–366 (1988).
Latimer et al., *Nucleic Acids. Res.* 17:1549–1561 (1989).
Kibler–Herzog et al., *Nucleic Acids. Res.* 18:3545–3555 (1990).
Sen et al., *Nature* 344:410–414 (1990).
Blackburn, *Nature* 350:569–573 (1991).
Durland et al., *Biochem.* 30:9246–9255 (1991).
Stahl et al., *FASEB J* 5:2799–2807 (1991).
Storey et al., *Nucleic Acids Res.* 19:4109–4114 (1991).
Xodo et al., *Nucleic Acids Res.* 19:5625–5631 (1991).
Young et al., *Proc. Natl. Acad. Sci.* (USA) 88:10023–10026 (1991.
Agrawal, *Trends in Biotechnol.* 10:152–158 (1992).
Cheng et al., *Prog. Biophys. Molec. Biol.* 58:225–257 (1992).
Giovannangeli et al., *Single–Stranded DNA as a Target for Triple Helix Formation*, J. Am. Chem. Soc. 113, 7775 (1991).
David J. D'Souza and Eric T. Kool, *Strong Binding of Single–Stranded DNA by Stem–Loop Oligonucleotides*, Journal of Biomolecular Structure & Dynamics (1992).
Lyamichev et al, J. Biomol. Structure and Dynamics, v. 3, N. 4, 1986, pp. 667–669.
Letai et al, Biochemistry, 1988, v. 27, pp. 9108–9112.
Zurita et al., *Proc. Natl. Acad. Sci* (USA) 84:2340–2344 (1987).

*Primary Examiner*—George G. Elliott
*Assistant Examiner*—Andrew Wang
*Attorney, Agent, or Firm*—McDonnell Boehnen Hulbert & Berghoff

[57] ABSTRACT

The invention provides novel oligonucleotides that form a duplex with a target nucleic acid and then form a triplex with the duplex formed between the oligonucleotide and the target nucleic acid.

4 Claims, 16 Drawing Sheets

ANTISENSE

ANTIGENE $G_4$ $A_4$

Oligo 2 - RNA, pH 5.0

Oligo 4 - DNA, pH 7.4

Oligo 4 - DNA, pH 7.4 + spermine

INTEGRATED OLIGONUCLEOTIDES

This application is a continuation of application Ser. No. 08/248,636 filed May 24, 1994, now abandoned, which was a continuation of application Ser. No. 08/008,000, filed Jan. 21, 1993 abandoned.

BACKGROUND OF THE INVENTION

1. Field of the Invention

The invention relates to synthetic oligonucleotides. More particularly, the invention relates to synthetic oligonucleotides that are useful in gene expression modulation.

2. Summary of the Related Art

Since Zamecnik and Stephenson, Proc. Natl. Acad. Sci. USA 75: 280–284 (1978) first demonstrated virus replication inhibition by synthetic oligonucleotides, great interest has been generated in oligonucleotides as therapeutic agents. In recent years the development of oligonucleotides as therapeutic agents and as agents of gene expression modulation has gained great momentum. The greatest development has been in the use of so-called antisense oligonucleotides, which form Watson-Crick duplexes with target mRNAs. Agrawal, Trends in Biotechnology 10: 152–158 (1992) extensively reviews the development of antisense oligonucleotides as antiviral agents.

Also important, but somewhat less developed is the so-called antigene oligonucleotide approach, in which oligonucleotides form triplexes with target DNA duplexes through Hoogsteen base pairing. Chang and Pettitt, Prog. Biophys. Molec. Biol. 58: 225–257 (1992) have recently reviewed developments in this latter approach. Triplex formation has been observed between DNA and various types of oligonucleotides. Cooney et al., Science 241: 456–459 (1988) teaches triplex formation between DNA and an oligodeoxynucleotide phosphodiester. Latimer et al., Nucleic Acids Res. 22: 1549–1561 (1989) discloses triplex formation involving oligodeoxynucleotide phosphorothioates. Kibler-Herzog et al., Nucleic Acids Res. 18: 3545–3555 (1990) discloses triplex formation involving short oligodeoxynucleotide methylphosphonates. Various base modifications that enhance triplex formation are also known, including C5-methylation of cytosine (Xodo et al., J. Molec. Biol. 19: 5625–5631 (1991)), use of the bicyclic cytosine analog, MODA (Young et al., Proc. Natl. Acad. Sci. USA 88: 10023–10100 (1991)), and use of a synthetic α-anomeric nucleotide (Praseuth et al., Proc. Natl. Acad. Sci. USA 85: 1349–1353 (1988)). Giovannangeli et al., J. Am. Chem. Soc. 113: 7775–7777 (1991) teaches that attachment of an acridine intercalator onto the 5'-end of a capped oligonucleotide also enhances triplex stability. Oligonucleotide-mediated triplex formation can cause inhibition of transcription, at least in vitro (see Cooney et al. and Young et al., supra).

Both the antisense and antigene oligonucleotide approaches have as their goal gene expression modulation that is beneficial in understanding gene expression and in therapeutic treatment of diseases or conditions involving gene expression. Two major characteristics of oligonucleotide compounds that are well suited to meet these goals are high specificity and an ability to interfere with gene expression upon binding. Enhancement of these characteristics is always desirable. There is, therefore, a need for new oligonucleotide compounds having even greater specificity and more stable complex formation, leading to increased ability to interfere with gene expression than existing compounds.

BRIEF SUMMARY OF THE INVENTION

The invention provides novel oligonucleotides that have greater specificity and more stable complex formation with target nucleic acids than existing oligonucleotides. Oligonucleotides according to the invention have a duplex forming region, which hybridizes to a single stranded target nucleic acid via Watson-Crick base-pairing, and a triplex forming region, which falls back on the duplex formed between the duplex forming region and the target nucleic acid, fitting in the major groove where it forms a triplex via Hoogsteen base-pairing with the target nucleic acid. The duplex forming region and triplex forming region are joined by a linker region, which may be an oligonucleotide loop or any flexible chemical structure that allows both the duplex forming region and the triplex forming region to bind to the target nucleic acid. The complex formed between the target nucleic acid and oligonucleotides according to the invention thus has characteristics similar to both the duplex structure of the antisense approach and the triplex structure of the antigene approach to gene expression modulation. Because the same oligonucleotide performs both duplex and triplex forming functions, this structure is called an integrated triplex and oligonucleotides according to the invention, which complex with target nucleic acids to form an integrated triplex, are called integrated oligonucleotides.

The increased specificity of integrated oligonucleotides arises from the fact that they must read the target nucleic acid twice, once initially through Watson-Crick base-pairing to form a duplex, and once again through Hoogsteen base-pairing to form a triplex. The increased stability of integrated complexes results from the increased number of hydrogen bonds formed between oligonucleotide and target nucleic acid. Integrated oligonucleotides according to the invention are useful for carrying out in vitro studies of the kinetics of duplex and triplex formation under varying parameters. They are also useful in gene expression modulation studies in tissue culture or animal models. Finally, integrated oligonucleotides according to the invention are useful as therapeutic agents in a novel approach having characteristics of both the antisense and antigene therapeutic approaches.

BRIEF DESCRIPTION OF THE DRAWINGS

In FIG. 3A, SEQ ID NOs: 4 and 5 the triplex Hoogsteen hydrogen bonding region extends for the same number of nucleotides as does the Watson-Crick base pairing region. In FIG. 3B, SEQ ID Nos: 16 and 39 the Hoogsteen hydrogen bonding region extends for a lesser number of nucleotides than does the Watson-Crick base-pairing region.

FIGS. 10A and B are a schematic representation of the RNase H hydrolysis pattern shown in FIG. 9 of target oligonucleotide, SEQ ID NO: 39 hybridized with SEQ ID NOs. 1, 2, 4, 12, 19, and 22, respectively. Thin arrows represent RNase H endonuclease activity. Broad arrows represent sites of inhibition of RNase H exonuclease activity.

DETAILED DESCRIPTION OF THE PREFERRED EMBODIMENTS

The invention relates to synthetic oligonucleotides that are useful in gene expression modulation. The invention provides synthetic oligonucleotides that have greater specificity and more stable complex formation with target nucleic acids than existing oligonucleotides.

Figure 1A:
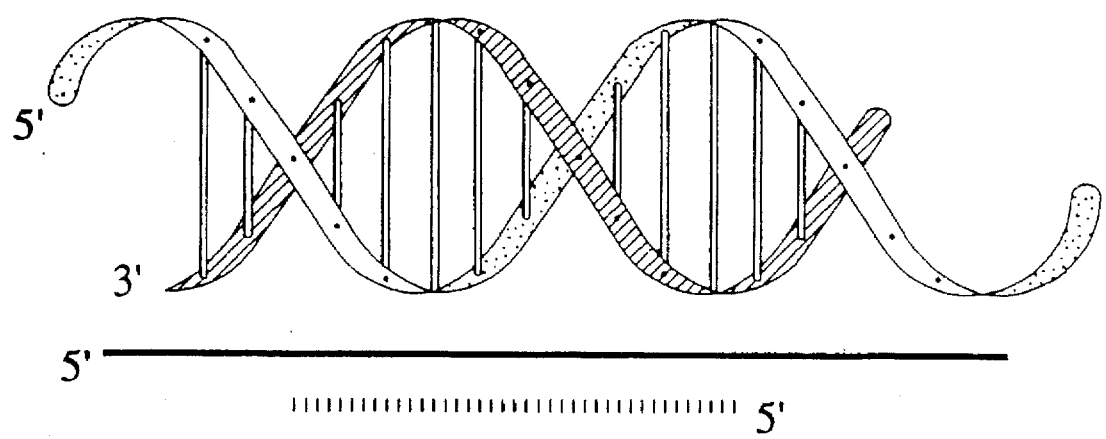
FIG. 1A shows the antisense approach and FIG. 1B shows the antigene approach to gene expression modulation.
Figure 1B:
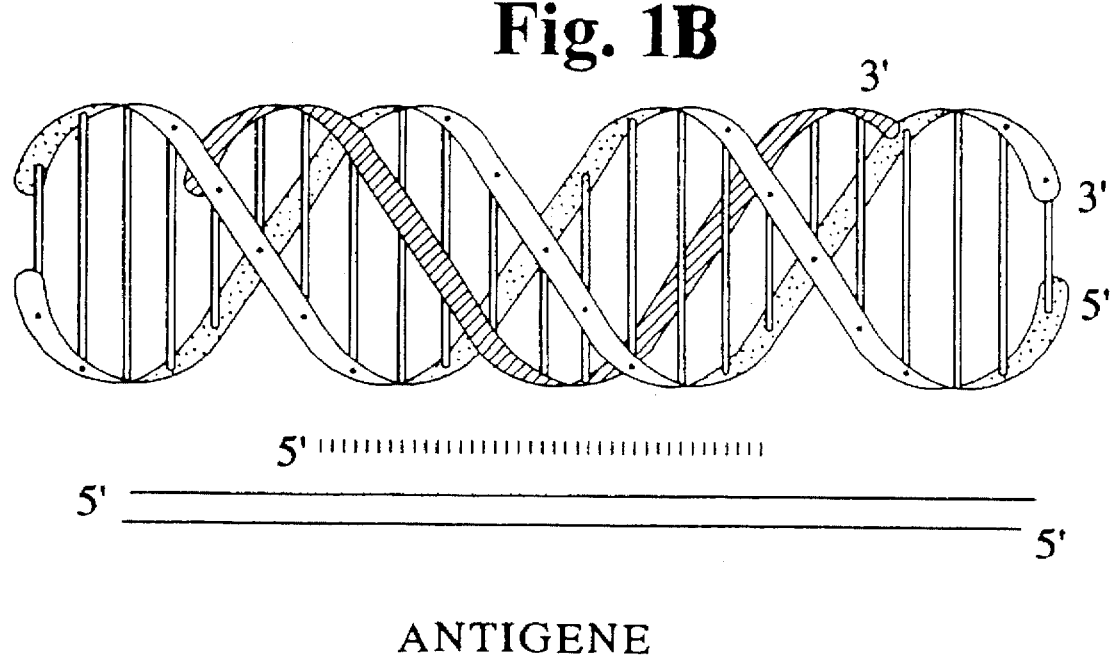
Figure 2A:
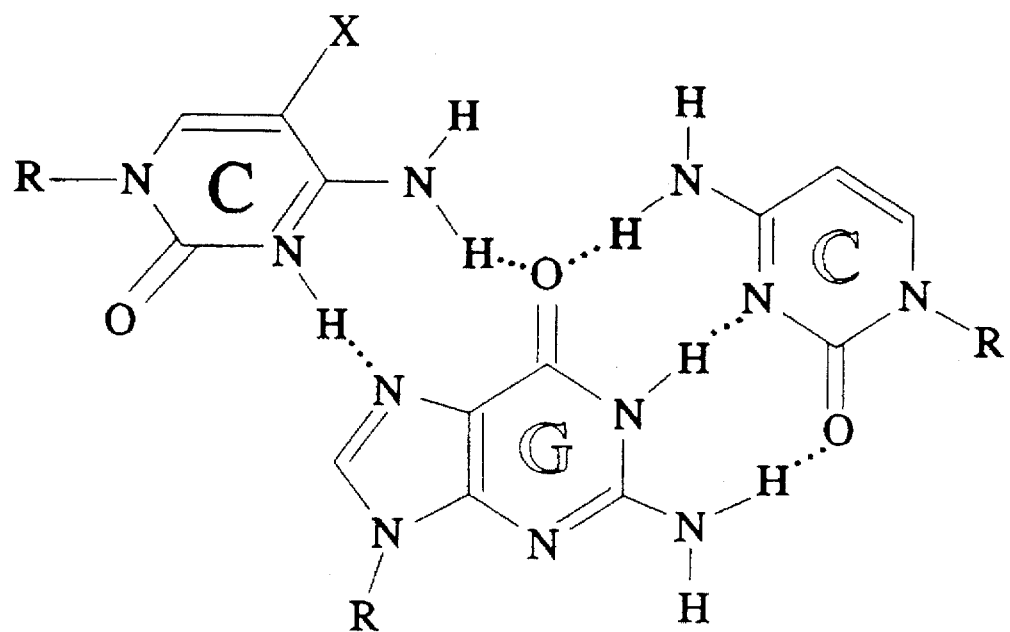
FIG. 2A shows C-G.$C^+$ hydrogen bonding
Figure 2B:
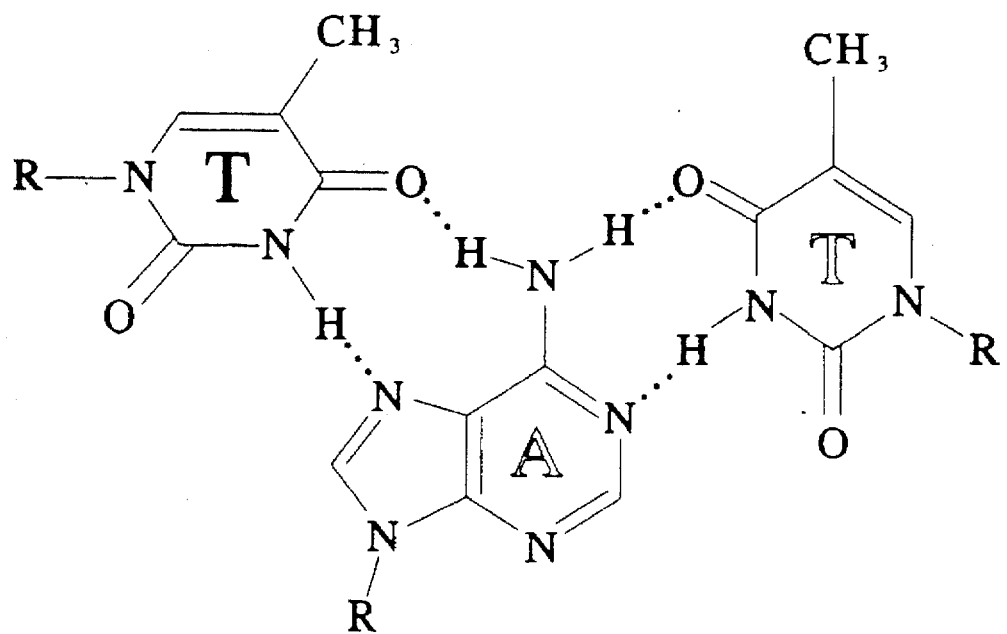
FIG. 2B shows T-A.T hydrogen bonding implicated in triplex formation.

Existing oligonucleotide-mediated approaches to gene expression modulation are the antisense approach and the antigene approach, which are illustrated in FIG. 1. In the antisense approach, the target nucleic acid is a single-stranded nucleic acid and the gene expression modulating agent is a complementary oligonucleotide. The complementary oligonucleotide and the target nucleic acid form a duplex by Watson-Crick base-pairing between the complementary bases. Modulation of gene expression presumably occurs by various mechanisms, including RNase H degradation of RNA, blocking of ribosome function on RNA, or blocking of enzyme function on RNA or DNA. In contrast, in the antigene approach, the target nucleic acid is a double-stranded nucleic acid and the gene expression modulating agent is an oligonucleotide that is capable of entering the major groove of the target duplex and forming Hoogsteen base pairs, such as those shown in FIG. 2, with one strand of the target duplex. This interaction results in triplex formation. Gene expression modulation presumably occurs via interference with transcription.

Figures 3A, 3B:
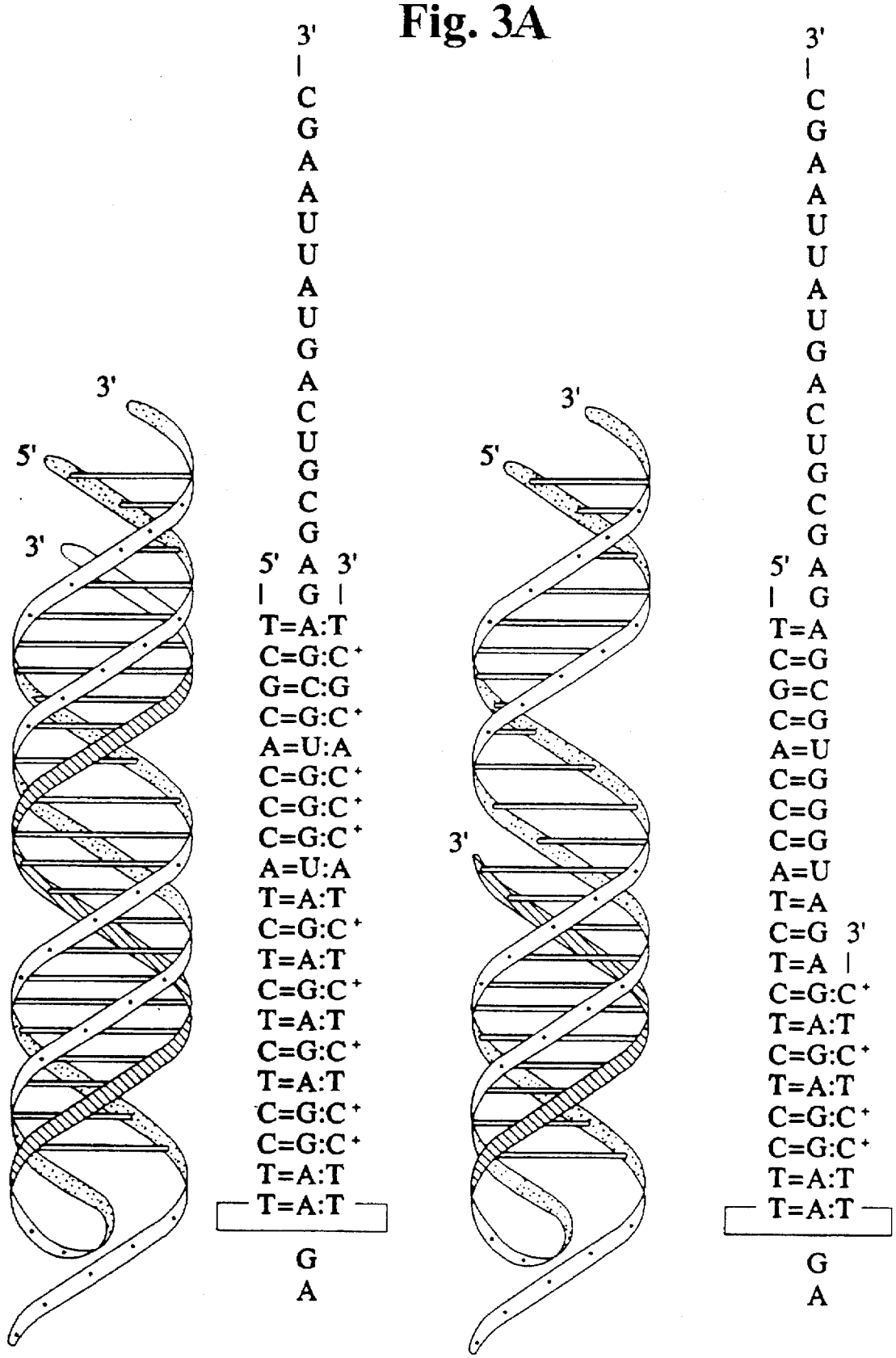
FIGS. 3A and 3B show integrated oligonucleotides according to the present invention, which bend to target nucleic acids by both Watson-Crick and Hoogsteen hydrogen bonding. Black strands represent the triplex forming region.

Oligonucleotides according to the invention have characteristics of both the antisense and antigene approaches. The target nucleic acid for oligonucleotides according to the invention is a single-stranded nucleic acid, as in the antisense approach. Oligonucleotides according to the invention have a duplex forming region, which is complementary to the target nucleic acid and forms a duplex with the target nucleic acid via Watson-Crick base-pairing between the complementary base pairs, just as in the antisense approach. However, oligonucleotides according to the invention also have a triplex forming region that has a nucleotide sequence that is of identical sequence but opposite polarity to the nucleotide sequence of the duplex forming region of the oligonucleotide, i.e., that is an inverted repeat. This triplex forming region interacts via Hoogsteen base-pairing with the target nucleic acid in the major groove of the duplex formed between the target nucleic acid and the duplex forming region of the oligonucleotide. The result of this interaction is the formation of a triplex. Such a complex, as shown in FIG. 3 for two oligonucleotides according to the invention and their targets is called an integrated triplex. Briefly stated, an integrated triplex is a complex formed between an oligonucleotide and a target nucleic acid, wherein the oligonucleotide first forms a duplex with the target nucleic acid and then the same oligonucleotide molecule falls back on and forms a triplex with the duplex formed between the target nucleic acid and the oligonucleotide. Because oligonucleotides according to the invention are capable of forming integrated triplexes with target nucleic acids, such oligonucleotides are hereby demarcated integrated oligonucleotides.

The fact that integrated oligonucleotides do form both duplexes and triplexes is demonstrated by independent lines of evidence. First, under conditions that allow Hoogsteen base-pairing involving a cytosine-containing triplex forming strand (pH 5.0, at which cytosine is protonated) integrated oligonucleotides form a complex with a target nucleic acid that upon thermal denaturation yields two distinct increases in $A_{260}$ (each increase being indicative of a denaturation event). The two $A_{260}$ increases occur at about the temperatures expected for thermal denaturation of triplexes and duplexes. The higher temperature (second) $A_{260}$ increase takes place at the expected temperature for disruption of a complex formed by Watson-Crick base-pairing, taking into account G+C content. The lower temperature (first) $A_{260}$ increase would be expected for disruption of a complex formed by the less thermodynamically stable Hoogsteen base-pairing. In contrast, when conditions are altered to prevent Hoogsteen base-pairing involving a cytosine-containing triplex forming strand (pH 7.4, at which cytosine is not protonated) only the higher temperature $A_{260}$ increase is observed. Moreover, at physiological concentrations of polyamines (3.0 mM spermine, which stabilizes triplex formation) the two $A_{260}$ increase pattern is restored.

Independent support for integrated triplex formation by integrated oligonucleotides comes from RNase H hydrolysis analysis. When a duplex is formed between an antisense oligonucleotide phosphodiester and a target RNA (Example 2, below), the RNA is rendered susceptible to RNase H digestion, first by RNase H endonuclease activity, then by RNase H exonuclease activity. However, when an integrated oligonucleotide phosphodiester is used the region that is involved in triplex formation does not inhibit or reduce RNase H endonuclease acitivity, but does inhibit RNase H exonuclease activity. Thus, when a duplex is formed between an antisense oligonucleotide or an exclusively duplex forming region of an integrated oligonucleotide and its target nucleic acid, RNase H exonuclease activity is not blocked, whereas in all regions where triplex is formed such activity is blocked. This suggests that if an integrated oligonucleotide that activates RNase H is desired, it is only necessary to leave a section of the oligonucleotide that is exclusively duplex forming and that contains nucleotides that activate RNase H (e.g., nucleotide phosphodiesters or phosphorothioates). The observed RNase H hydrolysis results are consistent with the notion that triplex formation makes the major groove of the duplex locally inaccessible to RNase H exonuclease activity, since triplex formation results from Hoogsteen base-pairing involving an oligonucleotide strand that occupies the major groove. Identical results should be obtained for integrated oligonucleotide phosphorothioates or chimerics, since it is known that oligonucleotide phosphorothioates in a chimeric oligonucleotide or alone also activate RNase H activity in a duplex with RNA (see U.S. Pat. No. 5,149,797, the teachings of which are incorporated by reference). Taken together, the observations of biphasic denaturation and triplex forming region-specific RNase H exonuclease inhibition strongly support integrated triplex formation between integrated oligonucleotides and their target nucleic acids. The implications of these findings include the following. They suggest that integrated oligonucleotides are capable of interfering with enzymatic activities that interact with the major groove of a nucleic acid duplex, which most likely includes any processive enzymatic activity, such as a polymerase activity. In addition, the zipper-like complex formed between integrated oligonucleotides and their target cannot be disrupted by ribozymes, in contrast to normal antisense oligonucleotides.

Integrated oligonucleotides generally have at least three structural features, a duplex forming region, a triplex forming region, and a linker region. For the intact integrated oligonucleotides and the various structural regions referred to herein, except where explicitly stated otherwise, structural features include, but are not limited to, having polymers of 5' to 3' linked ribonucleosides, 2' substituted ribonucleosides, and/or deoxyribonucleotides; wherein the internucleotide linkages may be a natural phosphodiester linkage or an artificial linkage, such as a phosphorothioate, phosphorodithioate, phosphoramidate, alkylphosphonate, akylphosphonothioate, sulfonate, carbamate and/or phosphotriester linkage. Moreover, such oligonucleotides encompass oligonucleotides having modifications on the bases and/or sugar residues as well as those having nuclease-resistance conferring substituents or bulky substituents at the 3' and/or 5' end. A sampling of integrated oligonucleotides is shown in Table I.

The duplex forming region of an integrated oligonucleotide is characterized by having a nucleotide sequence that is sufficiently complementary to a target nucleic acid sequence to hybridize to the target nucleic acid sequence under experimental or physiological conditions. Preferably, the duplex forming region has from about 8 to about 50 nucleotides, and most preferably has from about 12 to about 35 nucleotides. The target nucleic acid can, for experimental purposes, have essentially any nucleotide sequence. For therapeutic or medical uses of integrated oligonucleotides, however, the duplex forming region will preferably have a nucleotide sequence that is sufficiently complementary to hybridize under physiological conditions to the nucleotide sequence of a nucleic acid that is involved in a particular disease state or physiological condition. A sampling of integrated oligonucleotides having HIV gag-complementary sequences in their duplex forming region is shown in Table I.

The triplex forming region of an integrated oligonucleotide is characterized by having a nucleotide sequence that is the mirror image of the duplex forming region. Put differently, the base sequence of the triplex forming region is an inverted repeat of all or a portion of the duplex forming region of the same integrated oligonucleotide (and thus an inverted complement of the target sequence), not taking into account any base modifications. The triplex forming region preferably has at least about 8 nucleotides and can be of any length up to the full length of the duplex forming region. In a preferred embodiment, the bases of the triplex forming region include 5-bromodeoxyuridine and/or 5-methylcytosine, each of which promote Hoogsteen base pairing at physiological pH. The bicyclic cytosine analog MODA, α-anomeric nucleotides and/or terminal acridines, other terminal intercalators, or DNA cutting or modifying agents such as EDTA-FeII, and cc-1065 may also be present in the triplex forming region to promote triplex stability or target nucleic acid destruction.

The linker region of integrated oligonucleotides is a flexible region that connects the duplex forming region and the triplex forming region. The linker region may be an oligonucleotide having from about 3 to about 10 nucleotides. In a preferred embodiment, the linker region is an oligonucleotide having about 5 nucleotides. Alternatively, the linker region can be some other flexible chemical structure, such as a substituted or unsubstituted alkyl or aryl group having about 4 to 20 carbon atoms (e.g., isopropyl, o-xylyl), or ribose or 1', 2'-dideoxyribose chains. In a preferred embodiment, the linker region is hexaethylene glycol. At a minimum, the linker region is a single covalent bond. Certain preferred embodiments of integrated oligonucleotides are shown in Table I, below.

TABLE I

Selected Integrated Oligos And An Antisense Control Oligo

| Duplex Forming Region | Loop or Linker Region | Triplex Forming Region | Seq. Oligo ID No. |
|---|---|---|---|
| 5' - CTCTCGCACCCATCTCTCTCCTTCT- | - CACAC- | - TCTTCCTCTCTCTAC | 1 |
| 5' - CTCTCGCACCCATCTCTCTCCTTCT- | - - - L*- - - - | - TCTTCCTCTCTCTAC | 2 |
| 5' - CATCTCTCTCCTTCT- | - CACAC- | - TCTTCCTCTC | 3 |
| 5' - TCGCACCCATCTCTCTCCTT- | - CTCTC- | - TTCCTCTCTCTACCCACGCT | 4 |
| 5' - TCGCACCCATCTCTCTCCTT- | - CTCTC- | - TTCCTCTCTCTACCCACGC | 5 |
| 5' - TCGCACCCATCTCTCTCCTT- | - CTCTC- | - TTCCTCTCTCTACCCACG | 6 |
| 5' - TCGCACCCATCTCTCTCCTT- | - CTCTC- | - TTCCTCTCTCTACCCAC | 7 |
| 5' - TCGCACCCATCTCTCTCCTT- | - CTCTC- | - TTCCTCTCTCTACCCA | 8 |
| 5' - TCGCACCCATCTCTCTCCTT- | - CTCTC- | - TTCCTCTCTCTACCC | 9 |
| 5' - TCGCACCCATCTCTCTCCTT- | - CTCTC- | - TTCCTCTCTCTACC | 10 |
| 5' - TCGCACCCATCTCTCTCCTT- | - CTCTC- | - TTCCTCTCTCTAC | 11 |
| 5' - TCGCACCCATCTCTCTCCTT- | - CTCTC- | - TTCCTCTCTCTA | 12 |

TABLE I-continued

Selected Integrated Oligos And An Antisense Control Oligo

| Duplex Forming Region | Loop or Linker Region | Triplex Forming Region | Seq. Oligo ID No. |
|---|---|---|---|
| 5' - TCGCACCCATCTCTCTCCTT - | - CTCTC - | - TTCCTCTCTCT | 13 |
| 5' - TCGCACCCATCTCTCTCCTT - | - CTCTC - | - TTCCTCTCTC | 14 |
| 5' - TCGCACCCATCTCTCTCCTT - | - CTCTC - | - TTCCTCTCT | 15 |
| 5' - TCGCACCCATCTCTCTCCTT - | - CTCTC - | - TTCCTCTC | 16 |
| 5' - TCGCACCCATCTCTCTCCTT - | - TCTCT - | - TTCCTCTCTCTACCCACGCT | 17 |
| 5' - TCGCACCCATCTCTCTCCTT - | - TCTCT - | - TTCCTCTCTCTACC | 18 |
| 5' - TCGCACCCATCTCTCTCCTT - | - TCTCT - | - TTCCTCTC | 19 |
| 3' - TTCCTCTCTCTACCCACGCT - | - TCTCT - | - TCGCACCCATCTCT | 20 |
| 3' - TTCCTCTCTCTACCCACGCT - | - TCTCT - | - TCGCACCC | 21 |
| 5' - CTCTCGCACCCATCTCTCTCCTTCT | | | 22 |

*Hexaethylene glycol

Figure 4:
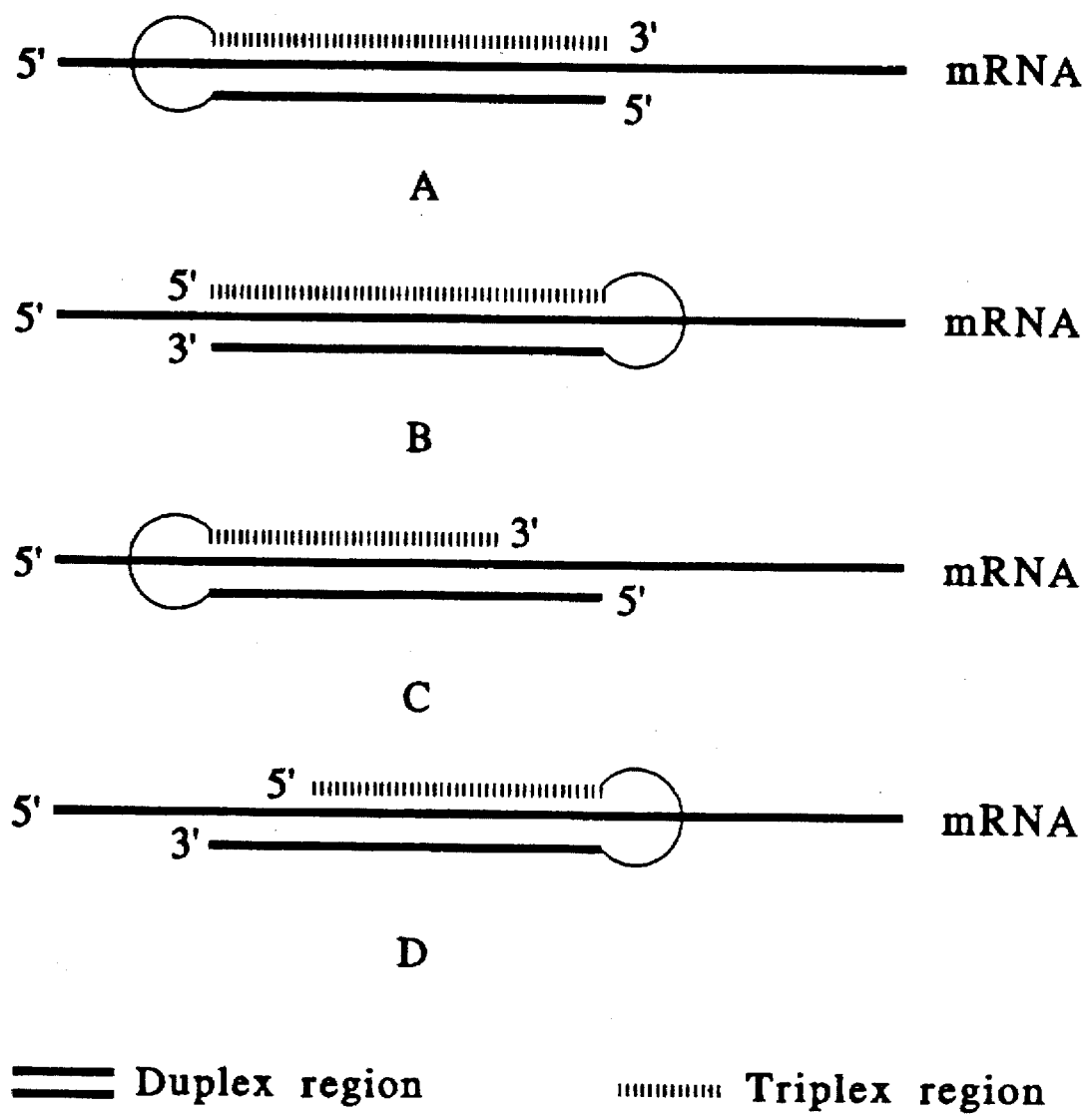
FIG. 4 shows four different types of integrated triplexes.

There are four different ways in which integrated oligonucleotides can form an integrated triplex with a target single stranded nucleic acid, depending on whether the duplex forming region is on the 5' to 3' side of the loop or linker region, as well as depending on the length of the triplex forming region. These four configurations are shown in FIG. 4. Of the oligonucleotides shown in Table I, numbers 4 and 17 form type A and/or B integrated triplexes, as shown in FIG. 4, whereas numbers 1–3, 5–16, 18 and 19 form type C integrated triplexes and numbers 20 and 21 form type D integrated triplexes (both as shown in FIG. 4).

Figure 5A:
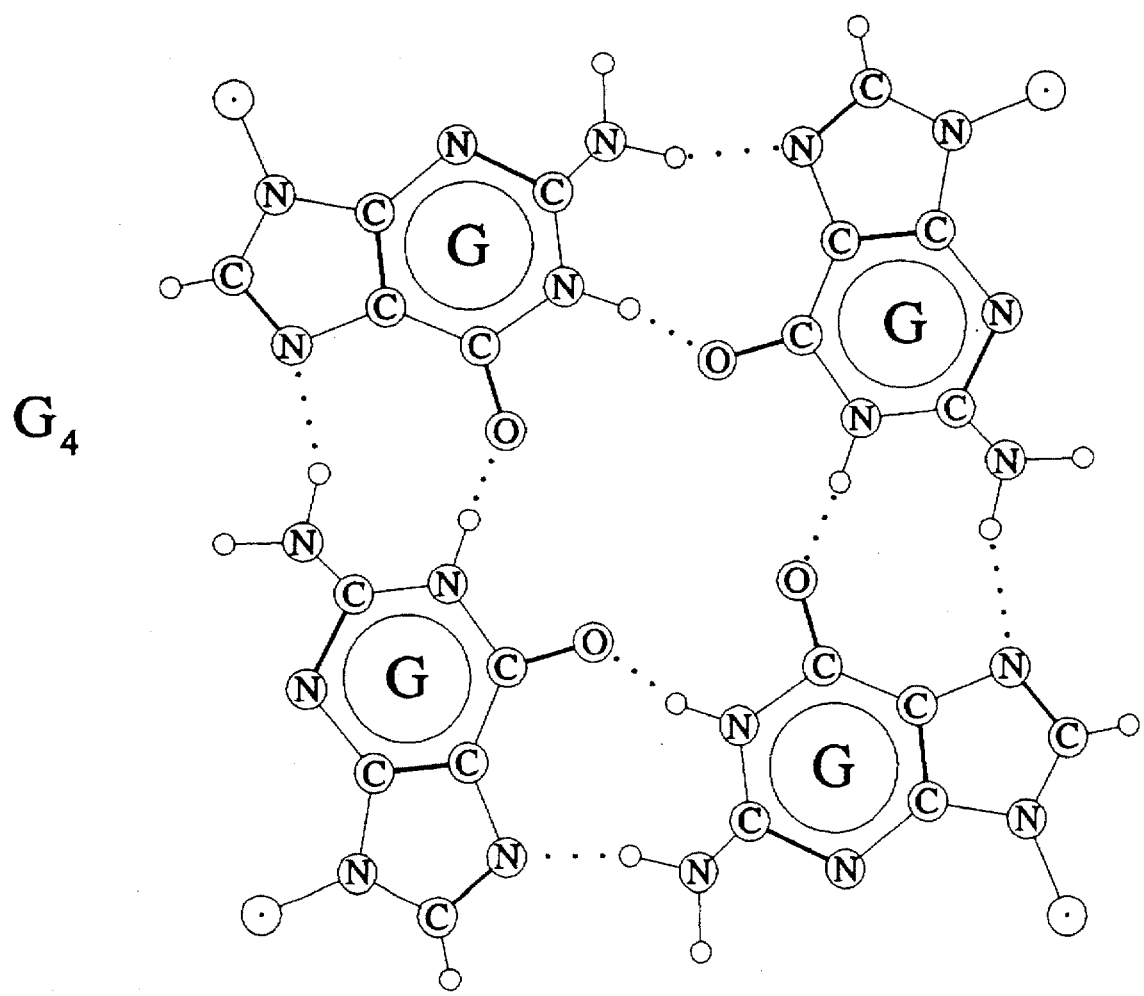
FIGS. 5A and 5B show hydrogen bonding patterns for G tetrads and A tetrads.
Figure 5B:
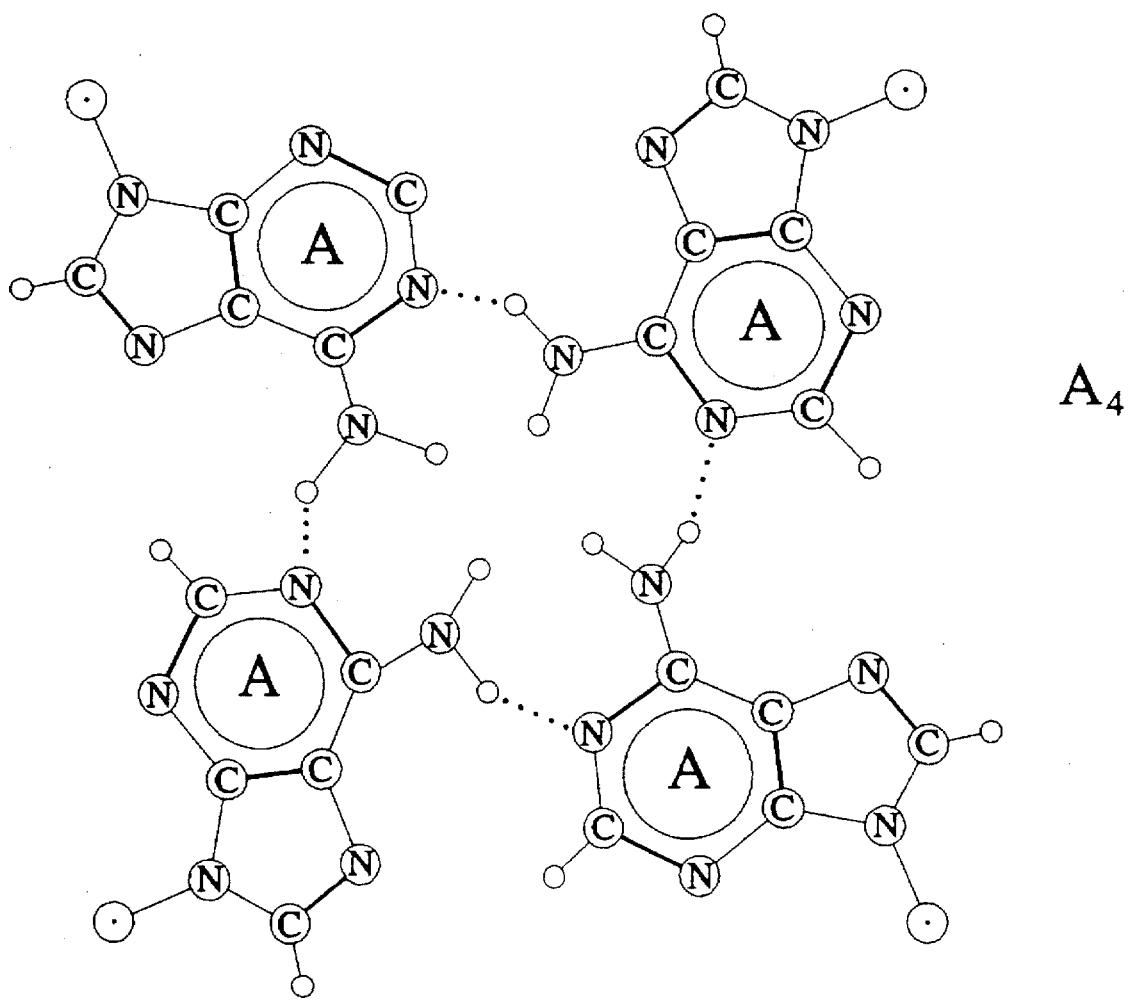

By careful selection of the target sequence, and hence of the sequences of the duplex and triplex forming regions of the integrated oligonucleotide, it should also be possible to create oligonucleotides that participate in tetraplex (a/k/a quadruplex) structures. Such oligonucleotides would be known as integrated tetraplex oligonucleotides, since the same nucleotide would participate with a target nucleic acid in different types of Hoogsteen base-pairing to form a tetraplex. The higher order tetraplex structures have been described for four side-by-side, distinct strands and for exclusively intramolecular formation (see e.g., Zimmerman et al., J. Mol. Biol. 92: 181–192 (1975); Lee et al., Nucleic Acids Res. 8: 4305–4320 (1980); Sen and Gilbert, Nature 334: 364–366 (1988) and 344: 410–414 (1990)). However, oligonucleotides having a structure that allows them to form tetraplex structures with single-stranded target nucleic acids have never been described. In such oligonucleotides, the target nucleic acid and the oligonucleotide should contain four contiguous G bases or A bases with adjacent G bases to allow formation of tetrads necessary for tetraplex formation. The G tetrad consists of four G bases hydrogen bonded in Hoogsteen fashion symmetrically disposed about a central axis, as shown in FIGS. 5A and B. The A tetrad, predicted by molecular modeling, consists of four A bases hydrogen bonded in similar Hoogsteen fashion, as also is shown in FIG. 5B. The disposition of 6-NH2 group in the center of the A4 tetrad destabilizes the structure and disfavors consecutive A4 tetrads in a tetraplex DNA. However, A4 tetrad formation could be favored by adjacent G4 tetrads through stabilization by favorable electrostatic interactions between 06 carbonyl oxygens of the G4 tetrad and the N6 amino protons of the A4 tetrad.

Figure 6A:
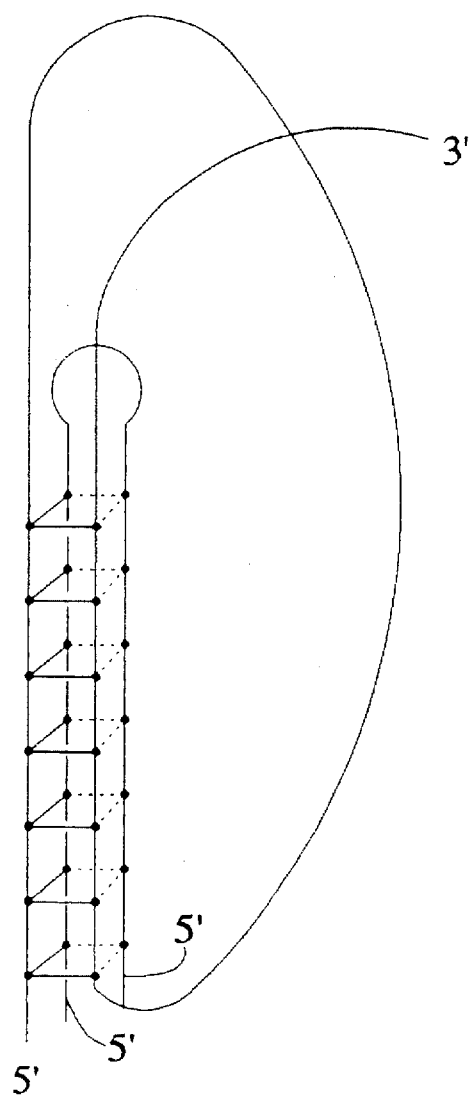
FIGS. 6A and 6B show two different molecular knots resulting from integrated tetraplex formation.
Figure 6B:
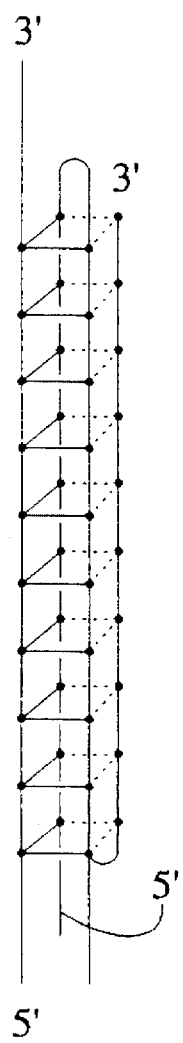

Integrated oligonucleotides according to the invention that are capable of forming integrated tetraplexes are useful for studying the tetraplex structure, the biological significance of which has recently generated some interest (see e.g., Blackburn, Nature 350: 569–573 (1991)). In addition, such oligonucleotides can interact with single stranded mRNA or duplex RNA or DNA to form complex molecular knots, as shown for mRNA in FIG. 6. These structures should strongly inhibit translation of the mRNA into protein or RNA or DNA replication or transcription, and should thus be useful for both cell culture gene expression modulation studies and as therapeutic agents.

Integrated oligonucleotides according to the invention can be synthesized according to any of the procedures known in the art for oligonucleotide synthesis. For example, U.S. Pat. No. 5,047,524, the teachings of which are hereby incorporated by reference, teaches phosphoramidite synthesis of oligonucleotides. Alternatively, U.S. Pat. No. 5,149,748, the teachings of which are hereby incorporated by reference, teaches an optimized H-phosphonate approach for oligonucleotide synthesis. For integrated oligonucleotides containing non-oligonucleotide linker regions, synthesis can still be carried out according to these procedures, provided that any hydroxyl groups are first protected by an appropriate protecting group, such as a dimethoxytrityl group, that any amino groups present be protected by an appropriate protective group, such as a trifluoroacetyl group, and that one end be linked to an appropriate coupling group, such as a β-cyanoethylphosphoramidite or H-phosphonate group.

Integrated oligonucleotides according to the invention are useful for a variety of purposes. First, they are useful for in vitro studies of nucleic acid triplex formation. In an integrated oligonucleotide it is possible to vary many parameters, such as internucleotide linkage types, base modifications, linker length and flexibility, etc. to study the kinetics of triplex formation and disruption, which may be a biologically important process. In addition, integrated oligonucleotides can be used in place of traditional antisense oligonucleotides in tissue culture and animal models for studying gene expression. In these systems, the increased specificity and complex stability of integrated oligonucleotides should be beneficial.

Finally, integrated oligonucleotides are useful as therapeutic agents for diseases or physiological conditions involving expression of specific genes. The disease or condition that a particular integrated oligonucleotide is useful for treating will depend upon the nucleotide sequence to which the duplex forming region is sufficiently complementary to hybridize under physiological conditions. In many cases the nucleic acid sequence will be a virus nucleic acid sequence. The use of antisense oligonucleotides to inhibit various viruses is well known, and has recently been reviewed in Agrawal, Tibtech 10: 152–158 (1992). The lessons learned from antisense antivirals can be applied to duplex forming regions. Viral nucleic acid sequences that hybridize to effective antisense oligonucleotides have been described for many viruses, including human immunodeficiency virus type 1 (U.S. Pat. No. 4,806,463, the teachings of which are herein incorporated by reference), Herpes simplex virus (U.S. Pat. No. 4,689,320, the teachings of which are hereby incorporated by reference), Influenza virus (U.S. Pat. No. 5,194,428, Ser. No. 07/516,275, allowed Jun. 30, 1002; the teachings of which are hereby incorporated by reference), and Human papilloma virus (Storey et al., Nucleic Acids Res. 19: 4109–4114 (1991)). Sequences hybridizing to any of these nucleic acid sequences can be used for the duplex forming region of integrated oligonucleotides, as can nucleotide sequences complementary to nucleic acid sequences from any other virus. Additional viruses that have known nucleic acid sequences against which integrated oligonucleotides can be prepared include, but are not limited to, Foot and Mouth Disease Virus (See Robertson et al., J. Virology 54: 651 (1985); Harris et al., J. Virology 36: 659 (1980)), Yellow Fever Virus (See Rice et al., Science 229: 726 (1985)), Varicella-Zoster Virus (see Davison and Scott, J. Gen. Virology 67: 2279 (1986), and Cucumber Mosaic Virus (See Richards et al., Virology 89: 395 (1978)). Alternatively, the duplex forming region can have a nucleotide sequence complementary to a nucleic acid sequence of a pathogenic organism. The nucleic acid sequences of many pathogenic organisms have been described, including the malaria organism, *Plasmodium falciparum*, and many pathogenic bacteria. Nucleotide sequences hybridizing to nucleic acid sequences from any such pathogenic organism can form the duplex forming region of integrated oligonucleotides. Examples of pathogenic eukaryotes having known nucleic acid sequences against which integrated oligonucleotides can be prepared include, but are not limited to *Trypanosoma brucei gambiense* and Leishmania (See Campbell et al., Nature 311: 350 (1984)), *Fasciola hepatica* (See Zurita et al., Proc. Natl. Acad. Sci. USA 84: 2340 (1987). Antifungal integrated oligonucleotides can be prepared using a duplex forming region having a nucleotide sequence that is complementary to a nucleic acid sequence from, e.g., the chitin synthetase gene, and antibacterial integrated oligonucleotides can be prepared using, e.g., the alanine racemase gene. In yet another embodiment, the duplex forming region of integrated oligonucleotides can have a nucleotide sequence complementary to a cellular gene or gene transcript, the abnormal expression or product of which results in a disease state. The nucleic acid sequences of several such cellular genes have been described, including prion protein (Stahl and Prusiner, FASEB J. 5: 2799–2807 (1991)), the amyloid-like protein associated with Alzheimer's disease (U.S. Pat. No. 5,015,570, the teachings of which are hereby incorporated by reference), and various well-known oncogenes and proto-oncogenes, such as c-myb, c-myc, c-abl, and n-ras. In addition, oligonucleotides that inhibit the synthesis of structural proteins or enzymes involved largely or exclusively in spermatogenesis, sperm motility, the binding of the sperm to the egg or any other step affecting sperm viability may be used as contraceptives for men. Similarly, contraceptives for women may be oligonucleotides that inhibit proteins or enzymes involved in ovulation, fertilization, implantation or in the biosynthesis of hormones involved in those processes. Hypertension can be controlled by oligonucleotides that suppress the synthesis of angiotensin converting enzyme or related enzymes in the renin/angiotensin system; platelet aggregation can be controlled by suppression of the synthesis of enzymes necessary for the synthesis of thromboxane A2 for use in myocardial and cerebral circulatory disorders, infarcts, arteriosclerosis, embolism and thrombosis; deposition of cholesterol in arterial wall can be inhibited by suppression of the synthesis of fattyacyl co-enzyme A: cholesterol acyl transferase in arteriosclerosis; inhibition of the synthesis of cholinephosphotransferase may be useful in hypolipidemia. There are numerous neural disorders in which integrated oligonucleotides can be used to reduce or eliminate adverse effects of the disorder. For example, suppression of the synthesis of monoamine oxidase can be used in Parkinson's disease; suppression of catechol o-methyl transferase can be used to treat depression; and suppression of indole N-methyl transferase can be used in treating schizophrenia. Suppression of selected enzymes in the arachidonic acid cascade which leads to prostaglandins and leukotrienes may be useful in the control of platelet aggregation, allergy, inflammation, pain and asthma. Suppression of the protein expressed by the multidrug resistance (mdr) gene, which is responsible for development of resistance to a variety of anti-cancer drugs and is a major impediment in chemotherapy may prove to be beneficial in the treatment of cancer. Nucleotide sequences complementary to nucleic acid sequences from any of these genes can be used for the duplex forming region of integrated oligonucleotides according to the invention, as can be oligonucleotide sequences complementary to any other cellular gene or gene transcript, the abnormal expression or product of which results in a disease state. Antisense regulation of gene expression in plant cells has been described in U.S. Pat. No. 5,107,065, the teachings of which are hereby incorporated by reference. Since the nucleotide sequence of the duplex forming region can be adapted to form Watson-Crick base pairs with essentially any gene, the therapeutic spectrum of integrated oligonucleotides should be very broad. Still, certain diseases are of particular interest. For example, a variety of viral diseases may be treated by integrated oligonucleotides, including AIDS, ARC, oral or genital herpes, papilloma warts, flu, foot and mouth disease, yellow fever, chicken pox, shingles, HTLV-leukemia, and hepatitis. Among fungal diseases treatable by integrated oligonucleotides are candidiasis, histoplasmosis, cryptococcocis, blastomycosis, aspergillosis, sporotrichosis, chromomycosis, dematophytosis and coccidioidomycosis. The method can also be used to treat rickettsial diseases (e.g., typhus, Rocky Mountain spotted fever), as well as sexually transmitted diseases caused by *Chlamydia trachomatis* or *Lymphogranuloma venereum*. A variety of parasitic diseases can be treated by integrated oligonucleotides including amebiasis, Chegas' disease, toxoplasmosis, pneumocystosis, giardiasis, cryptosporidiosis, trichomoniasis, and *Pneumocystis carini* pneumonia; also worm (helminthic diseases) such as ascariasis, filariasis, trichinosis, schistosomiasis and nematode or cestode infections. Malaria can be treated by integrated oligonucleotides regardless of whether it is caused by *P. falciparum*, *P. vivax*,

*P. orale*, or *P. malariae*. The infectious diseases identified above can all be treated by integrated oligonucleotides because the infectious agents for these diseases are known and thus integrated oligonucleotides according to the invention can be prepared, having a target forming region that has a nucleotide sequence that hybridizes to a nucleic acid sequence that is an essential nucleic acid sequence for the propagation of the infectious agent, such as an essential gene.

The following examples are intended to further illustrate certain preferred embodiments of the invention and are not limiting in nature.

EXAMPLE 1

Spectrophotometric Determination of Integrated Triplex Formation

Target RNA or DNA and an integrated oligonucleotide (0.2 $A_{260}$ units each) were dried, then dissolved together in 500 μl 100 mM sodium acetate/1 mM EDTA. The solution was heated to 80° C. for 30 minutes and cooled to room temperature slowly, then incubated at 4° C. for about 12 hours. The solution was then heated to 80°–90° C. at a rate of 0.5° C./minute, during which $A_{260}$ measurements were taken. Increases in $A_{260}$ were indicative of helix disruption. The results of these studies are summarized in Table II, below.

Figure 7A:
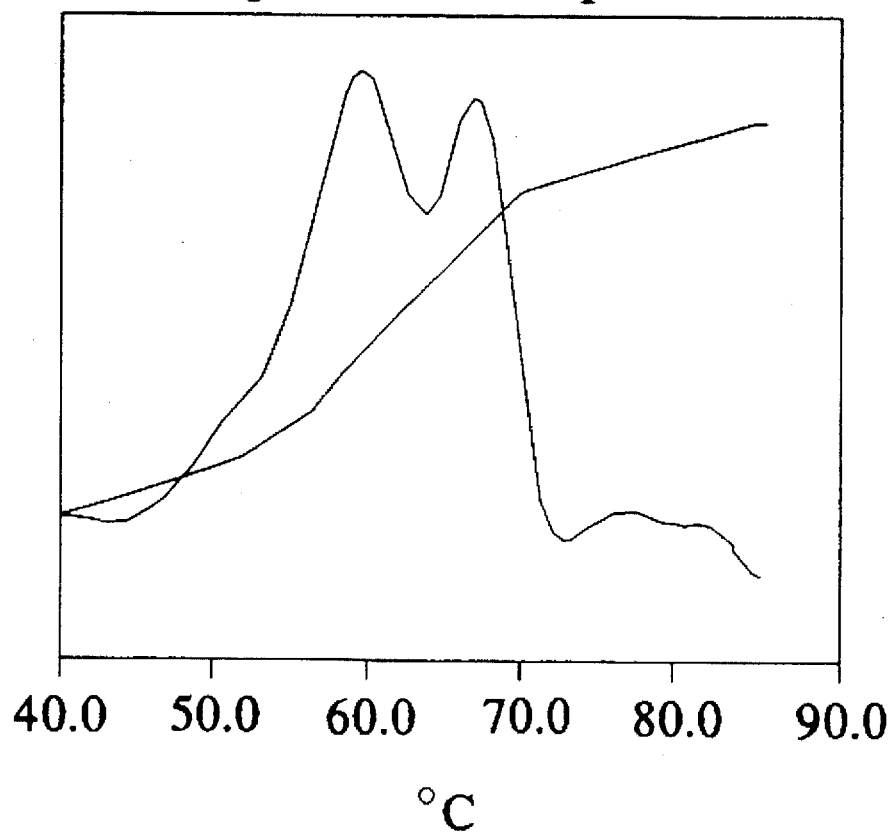
FIGS. 7A–C show spectrophotometric results demonstrating integrated triplex formation between a target RNA or DNA and an integrated oligonucleotide according to the invention.
Figure 7B:
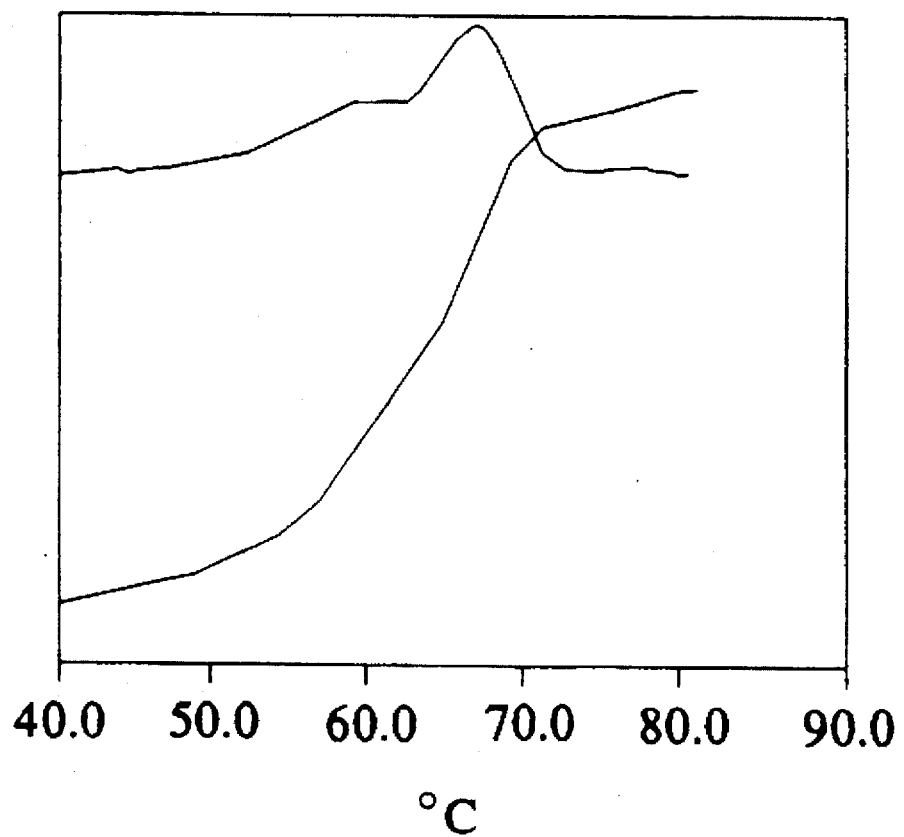
Figure 7C:
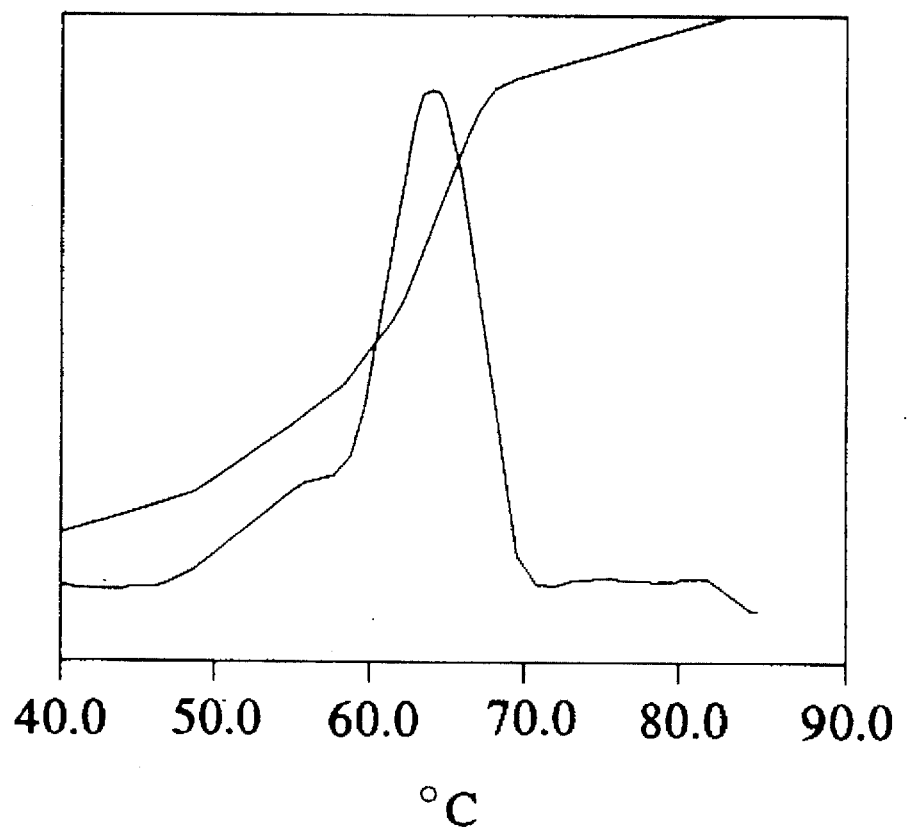

Initial studies were performed in a sodium acetate buffer of pH 5.0, in which cytosine is protonated and capable of forming Hoogsteen base pairs with guanine. In these studies, oligonucleotides 1 and 2 (see Table I) bound to complementary RNA or DNA with two distinct $A_{260}$ transitions (See FIGS. 7A–C). Oligonucleotide 1 with complementary DNA showed $A_{260}$ transitions at 59.5° and 65.8° C. Oligonucleotide 2, having a hexaethylene glycol linker showed $A_{260}$ transitions with complementary DNA at 58.8° and 65.6° C. and with complementary RNA at 55.3° and 64.3° C. These results indicate that oligonucleotides 1 and 2 form integrated triplexes, i.e., both duplexes and triplexes with RNA and DNA, with duplexes being disrupted at about the expected temperatures and triplexes being disrupted earlier at lower temperatures.

To further test this interpretation of the results, another experiment was performed under conditions that were identical to the initial studies, except that the sodium acetate buffer was of pH 7.4. Under these conditions, the higher temperature $A_{260}$ transition was observed, but the lower temperature $A_{260}$ transition disappeared. This further supports formation and disruption of duplexes and triplexes as an explanation for the two transitions observed at pH 5.0, since at pH 7.4 cytosine is not protonated and thus cannot form Hoogsteen hydrogen bonds necessary for triplex formation (See FIG. 2).

Figure 8A:
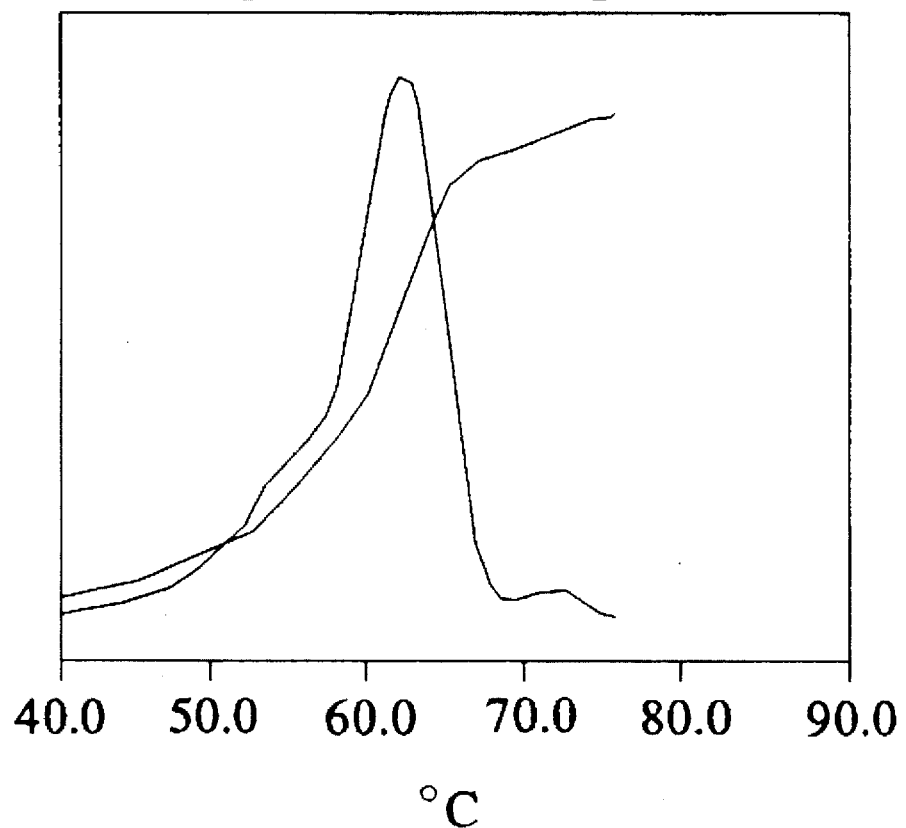
FIGS. 8A–C show spectrophotometric results demonstrating integrated triplex formation between a target DNA and an integrated oligonucleotide according to the invention at pH 5.0 (FIG. 8A), but not at pH 7.4 (FIG. 8B), except in the presence of the polyamine spermine (FIG. 8C).
Figure 8B:
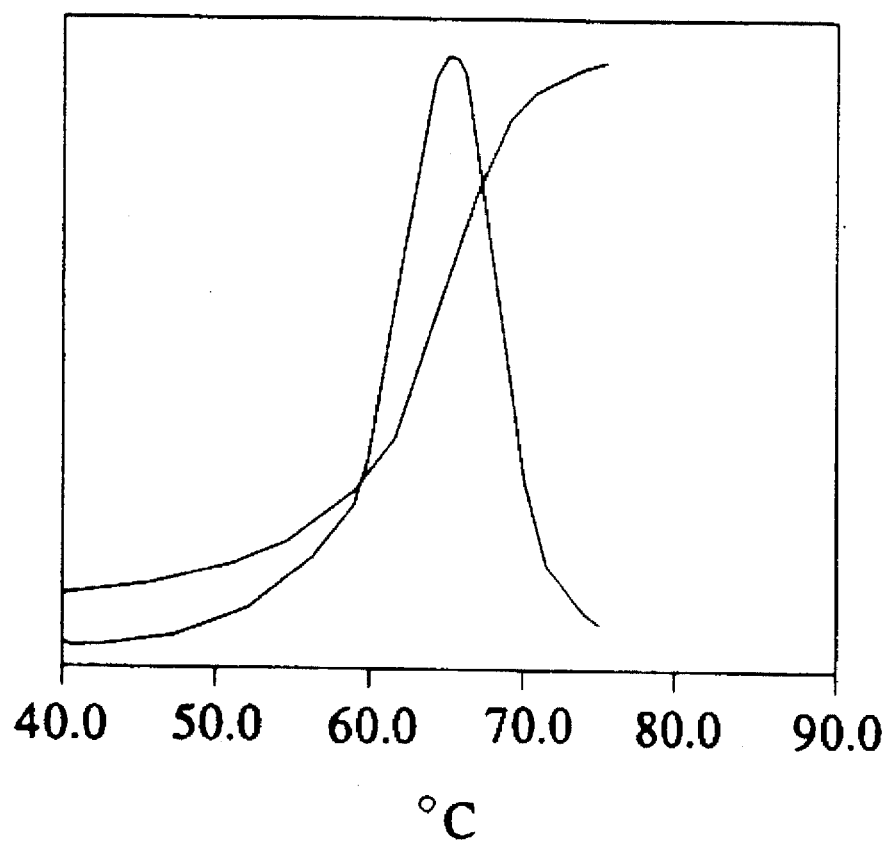
Figure 8C:
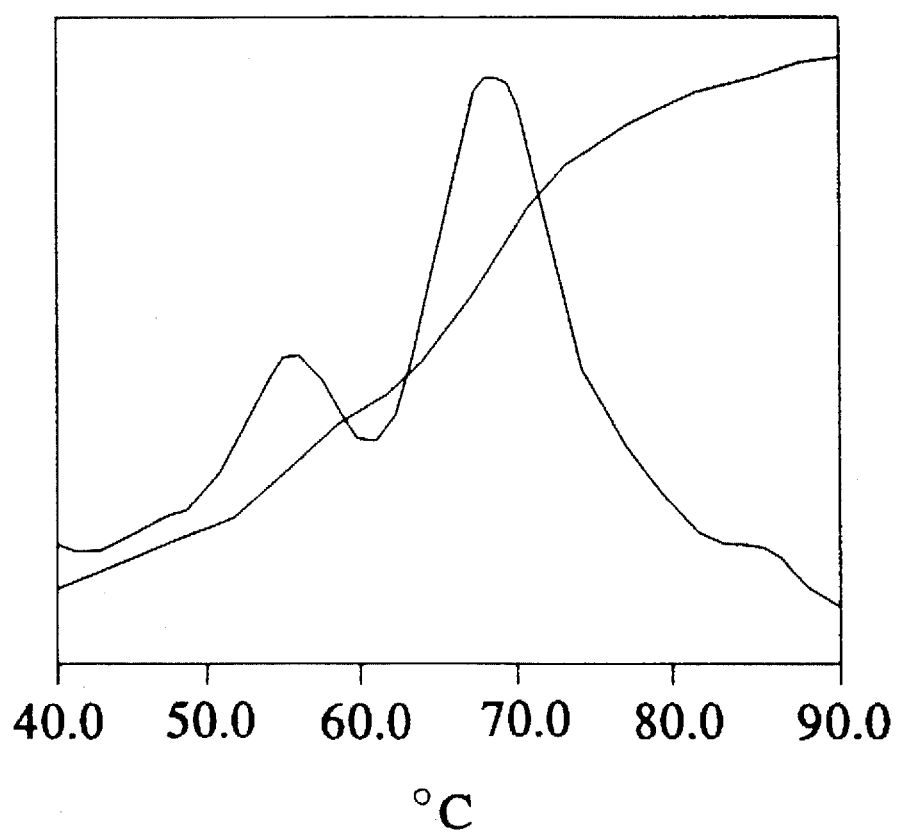

Finally, to test whether these oligonucleotides can form integrated triplexes with complementary RNA or DNA under physiological conditions, an experiment was performed using oligonucleotide 4 (see Table I) under conditions that were identical to the initial studies, except that the sodium acetate buffer was of pH 7.4 and contained 3.0 mM spermine. Under these conditions, the two distinct $A_{260}$ transitions were restored (See FIGS. 8A–C). These results indicate that these oligonucleotides can indeed form integrated triplexes under physiological conditions, which include millimolar quantities of polyamines.

TABLE II

Spectrophotometric Analysis Of Integrated Triplexes

| Sequence No. | Tm. °C.* Triplex DNA | Triplex RNA | Duplex DNA | Duplex RNA | Conditions |
|---|---|---|---|---|---|
| 1 | 58.8 | — | 65.6 | — | pH 5.0 |
| 2 | 59.5 | — | 65.8 | 64.3 | pH 5.0 |
| 4 | 56.5 | — | 61.3 | — | pH 5.0 |
| 4 | N | — | 65.8 | — | pH 7.4 |
| 4 | 56.0 | — | 68.8 | — | pH 7.4 + S |

*Average of two values.

EXAMPLE 2

RNase H Hydrolysis Analysis of Duplexes and Integrated Triplexes

To examine the effect of integrated triplex formation on enzymatic activity that utilizes RNA as a substrate, RNase H hydrolysis analysis was conducted. For these studies, a 39 ribonucleotide (RNA) having an HIV-1 gag RNA sequence was used. The 39-mer, 5'-AGAAGGAGAGAGAUGGGUG CGAGAGCGUCAGUAUUAAGC-3' SEQ ID NO 23, was 5'-end labelled with $^{32}$P and incubated with different concentrations of exclusively duplex-forming (antisense) or integrated oligonucleotides (DNA) in 30 μl 20 mM Tris.HCl, pH7.5/10 mM $MgCl_2$/100 mMKCl, 0.1 mM DTT, 3 mM spermine 5% sucrose (w/v), and 40 units RNasin (Promega) at 40° C. for 12 hours. A 7 μl aliquot was then removed as a control and 10 μl (0.8 units) *E. coli* RNase H (Promega) was added to the remainder, which was then incubated at room temperature. Aliquots were removed 1, 10 and 20 minutes after beginning RNase H treatment. Control and experimental aliquots were then analyzed by 20% denaturing PAGE.

Figure 9:
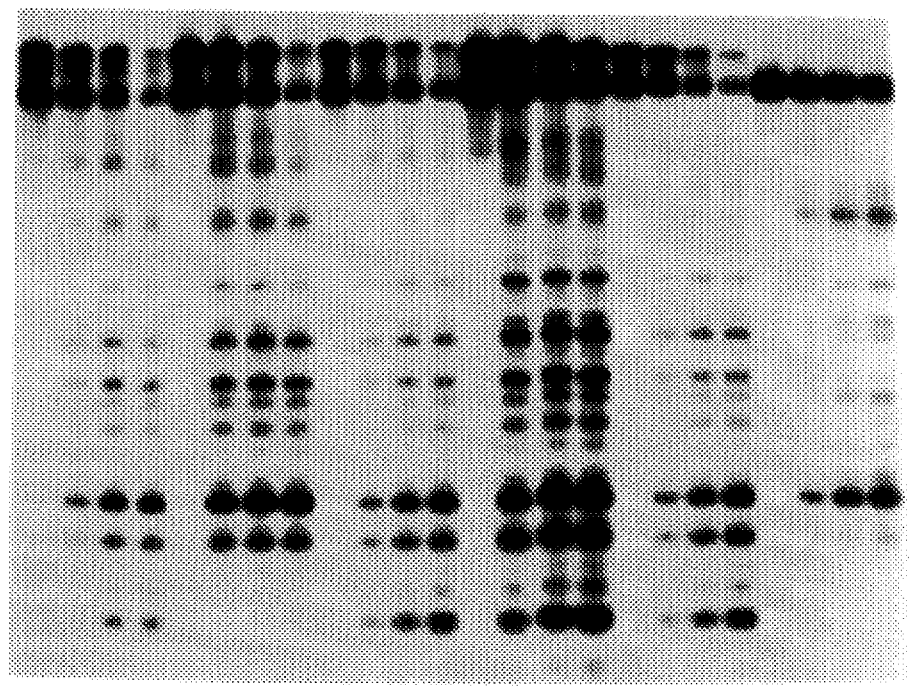
FIG. 9 shows RNase H hydrolysis patterns for RNA target molecules bound to integrated oligonucleotides according to the invention or to a control duplex-forming oligonucleotide.
Figure 10A:
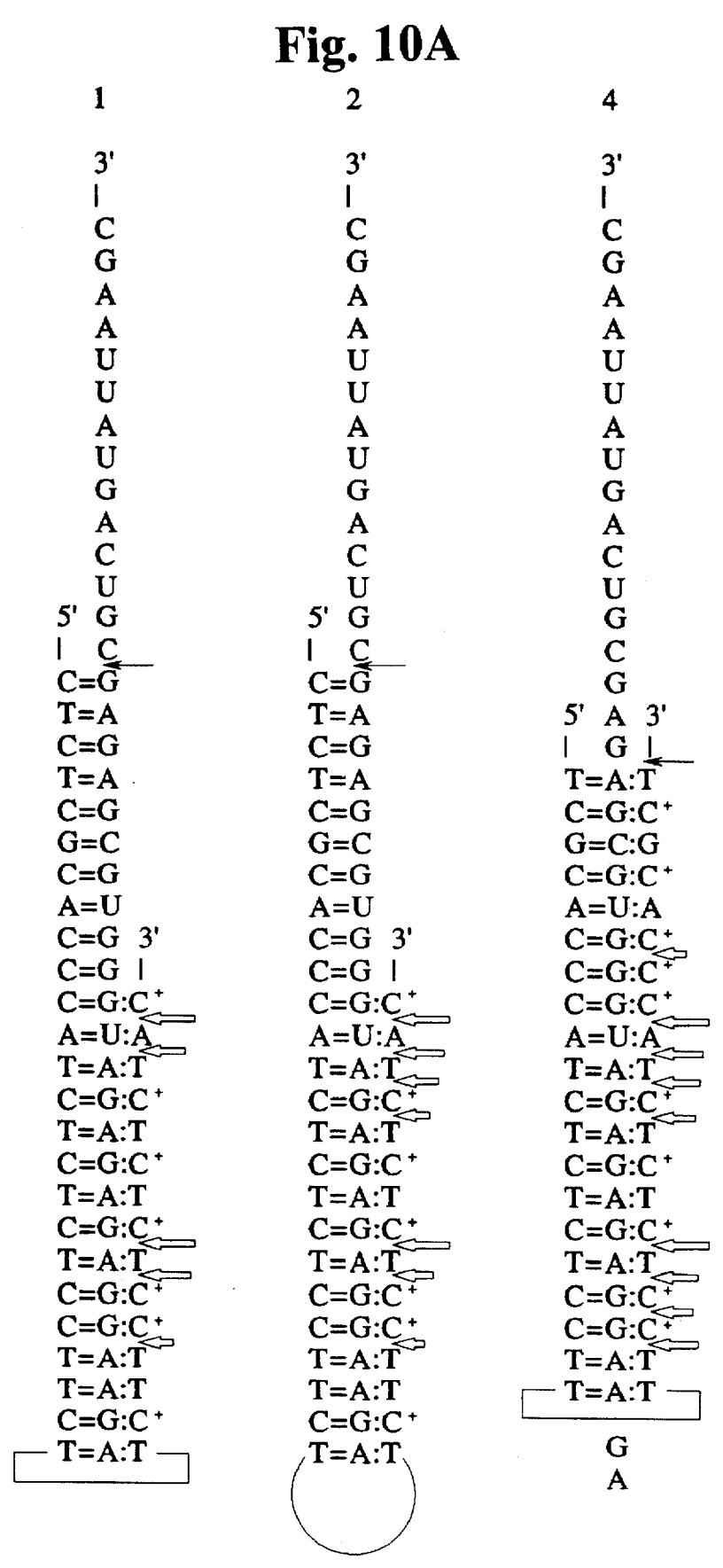
Figure 10B:
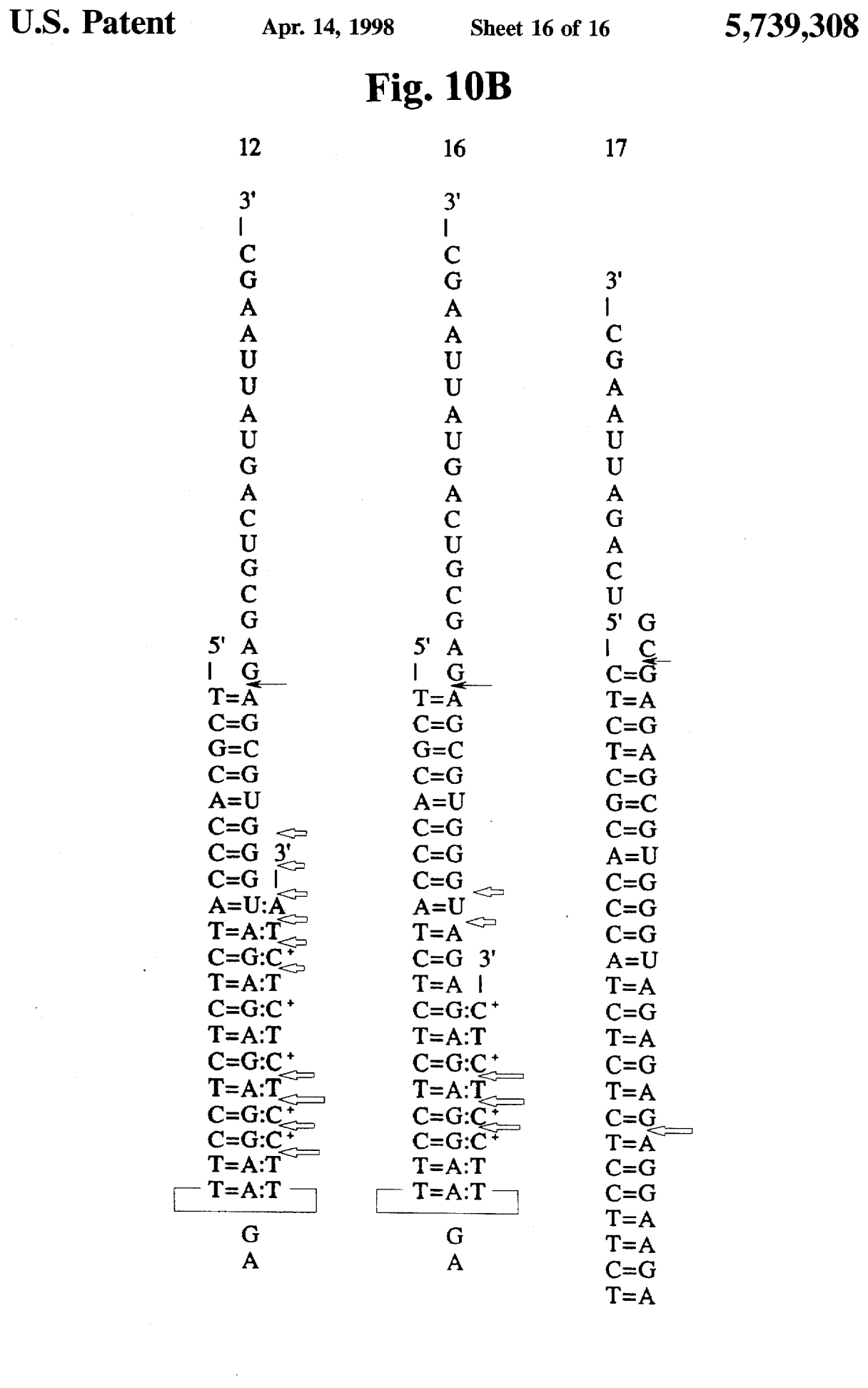

FIG. 9 shows the autoradiogram obtained from these experiments. These results demonstrate that integrated triplex formation did not inhibit the endonuclease activity of RNase H, but did inhibit the exonuclease activity of RNase H. These results are shown schematically in FIGS. 10A and B, in which broad arrows indicate observed RNase H exonuclease inhibition sites and thin arrows indicate the site of RNase H endonuclease activity. When RNase H acts on its substrate, it first makes an endonucleolytic cut in the RNA at the duplex and single strand junction near the 5' end of the oligonucleotide, then degrades the RNA by exonucleolytic activity from the endonucleolytic cleavage site. In the exclusively duplex forming control (oligo 22), only two bands are seen in FIG. 9, one from RNase H endonucleolytic activity (slow migrating band) and one from RNase H exonuclease activity (faster migrating band). No intermediate migrating bands would be observed due to exonuclease activity in the absence of inhibition. In contrast, several intermediate bands are present whenever integrated oligonucleotides are used. These bands indicate inhibition of RNase H exonuclease activity at several sites, due to blocking of the major groove by triplex formation.

We claim:

1. An integrated oligonucleotide having from about 16 to about 110 nucleotides, wherein said oligonucleotide includes a duplex forming region that forms a duplex with a target nucleic acid, a triplex forming region that forms a triplex with the duplex formed between the duplex forming region and the target nucleic acid, and a linker region connecting the duplex forming region and the triplex forming region, wherein the duplex forming region is from about 8 to about 50 nucleotides in length and has at least one C nucleotide, and wherein each of the duplex- and triplex-forming regions is comprised of both purine and pyrimidine nucleotides, and the triplex has a melting temperature above 56° C., provided that there is no intercalating agent covalently bound to the integrated oligonucleotide's 5' end and neither the duplex- nor triplex-forming regions contain two or more consecutive purine nucleotides.

2. The integrated oligonucleotide according to claim 1, wherein the duplex forming region has from about 12 to about 35 nucleotides.

3. The integrated oligonucleotide according to claim 1, wherein the triplex forming region is an inverted repeat of from about 8 to about 50 nucleotides of the duplex forming region.

4. The integrated oligonucleotide, according to claim 3, wherein the linker region comprises a chemical substituent selected from the group consisting of an oligonucleotide, a substituted or unsubstituted alkyl or aryl group having from about 4 to about 20 carbon atoms, and a chemical bond.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

CTCTCGCACC CATCTCTCTC CTTCTCACAC TCTTCCTCTC TCTAC     45

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

CTCTCGCACC CATCTCTCTC CTTCTTCTTC CTCTCTCTAC     40

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:3:

CATCTCTCTC CTTCTCACAC TCTTCCTCTC     30

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

TCGCACCCAT CTCTCTCCTT CTCTCTTCCT CTCTCTACCC ACGCT         45

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:5:

TCGCACCATC TCTCTCCTTC TCTCTTCCTC TCTCTACCCA CGC           43

( 2 ) INFORMATION FOR SEQ ID NO:6:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

TCGCACCCAT CTCTCTCCTT CTCTCTTCCT CTCTCTACCC ACG           43

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:7:

TCGCACCCAT CTCTCTCCTT CTCTCTTCCT CTCTCTACCC AC            42

( 2 ) INFORMATION FOR SEQ ID NO:8:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

TCGCACCCAT CTCTCTCCTT CTCTCTTCCT CTCTCTACCC A             41

( 2 ) INFORMATION FOR SEQ ID NO:9:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:9:

TCGCACCCAT CTCTCTCCTT CTCTCTTCCT CTCTCTACCC      40

( 2 ) INFORMATION FOR SEQ ID NO:10:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:10:

TCGCACCCAT CTCTCTCCTT CTCTCTTCCT CTCTCTACC      39

( 2 ) INFORMATION FOR SEQ ID NO:11:

( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:11:

TCGCACCCAT CTCTCTCCTT CTCTCTTCCT CTCTCTAC      38

( 2 ) INFORMATION FOR SEQ ID NO:12:

( i ) SEQUENCE CHARACTERISTICS:
            ( A ) LENGTH: 37 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:12:

TCGCACCCAT CTCTCTCCTT CTCTCTTCCT CTCTCTA      37

( 2 ) INFORMATION FOR SEQ ID NO:13:

( i ) SEQUENCE CHARACTERISTICS:
            ( A ) LENGTH: 36 base pairs ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:13:

TCGCACCCAT CTCTCTCCTT CTCTCTTCCT CTCTCT                                    36

( 2 ) INFORMATION FOR SEQ ID NO:14:

( i ) SEQUENCE CHARACTERISTICS:
                    ( A ) LENGTH: 35 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:14:

TCGCACCCAT CTCTCTCCTT CTCTCTTCCT CTCTC                                     35

( 2 ) INFORMATION FOR SEQ ID NO:15:

( i ) SEQUENCE CHARACTERISTICS:
                    ( A ) LENGTH: 34 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:15:

TCGCACCCAT CTCTCTCCTT CTCTCTTCCT CTCT                                      34

( 2 ) INFORMATION FOR SEQ ID NO:16:

( i ) SEQUENCE CHARACTERISTICS:
                    ( A ) LENGTH: 33 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:16:

TCGCACCCAT CTCTCTCCTT CTCTCTTCCT CTC                                       33

( 2 ) INFORMATION FOR SEQ ID NO:17:

( i ) SEQUENCE CHARACTERISTICS:
                    ( A ) LENGTH: 45 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:17:

TCGCACCCAT CTCTCTCCTT TCTCTTTCCT CTCTCTACCC ACGCT 45

( 2 ) INFORMATION FOR SEQ ID NO:18:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:18:

TCGCACCCAT CTCTCTCCTT TCTCTTTCCT CTCTCTACC 39

( 2 ) INFORMATION FOR SEQ ID NO:19:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:19:

TCGCACCCAT CTCTCTCCTT TCTCTTTCCT CTC 33

( 2 ) INFORMATION FOR SEQ ID NO:20:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:20:

TTCCTCTCTC TACCCACGCT TCTCTTCGCA CCCATCTCT 39

( 2 ) INFORMATION FOR SEQ ID NO:21:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO (i v) ANTI-SENSE: YES (x i) SEQUENCE DESCRIPTION: SEQ ID NO:21:

TTCCTCTCTC TACCCACGCT TCTCTTCGCA CCC    33

(2) INFORMATION FOR SEQ ID NO:22:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:22:

CTCTCGCACC CATCTCTCTC CTTCT    25

(2) INFORMATION FOR SEQ ID NO:23:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (i i) MOLECULE TYPE: RNA (genomic)

(i i i) HYPOTHETICAL: NO (i v) ANTI-SENSE: NO (x i) SEQUENCE DESCRIPTION: SEQ ID NO:23:

AGAAGGAGAG AGAUGGGUGC GAGAGCGUCA GUAUUAAGC    39